United States Patent
Sale

[19]

[11] Patent Number: 6,053,732
[45] Date of Patent: Apr. 25, 2000

[54] DENTAL PROPHYLAXIS ANGLE AND A PIVOTABLE PROPHY CUP THEREFORE

[75] Inventor: David William Sale, Heber Springs, Ark.

[73] Assignee: Professional Dental Technologies, Inc., Batesville, Ak.

[21] Appl. No.: 09/020,059

[22] Filed: Feb. 6, 1998

Related U.S. Application Data

[63] Continuation-in-part of application No. 08/718,750, Sep. 23, 1996, abandoned.

[51] Int. Cl.[7] .................................................... A61C 3/06
[52] U.S. Cl. ............................................ 433/125; 433/166
[58] Field of Search ................................... 433/114, 115, 433/125, 126, 166

[56] References Cited

U.S. PATENT DOCUMENTS

| | | | |
|---|---|---|---|
| 3,163,934 | 1/1965 | Wiseman | 433/115 |
| 3,472,045 | 10/1969 | Nelsen et al. | 433/125 |
| 3,478,433 | 11/1969 | Richmond | 433/115 |
| 4,123,845 | 11/1978 | Fattaleh | 433/126 |
| 4,348,180 | 9/1982 | Schuss | 433/126 |
| 5,040,978 | 8/1991 | Falcon et al. | 433/125 |
| 5,120,220 | 6/1992 | Butler | 433/125 |
| 5,352,119 | 10/1994 | Sakurai | 433/125 |
| 5,482,461 | 1/1996 | Yale | 433/125 |
| 5,507,644 | 4/1996 | Kivlighan, Jr. | 433/166 |
| 5,642,995 | 7/1997 | Bailey | 433/115 |

FOREIGN PATENT DOCUMENTS

| | | | |
|---|---|---|---|
| 24343 | 6/1911 | United Kingdom . | |
| 2223977 | 4/1990 | United Kingdom | 433/126 |

*Primary Examiner*—Ralph A. Lewis
*Attorney, Agent, or Firm*—Nims, Howes, Collison Hansen & Lackert

[57] ABSTRACT

In a dental prophylaxis angle, an angle housing defines a main passageway and an ancillary passageway communicating therewith and extending at an substantial angle thereto. A drive shaft extends through the main passageway, while a cup holder is rotatably disposed in the ancillary passageway, the cup holder being drivingly coupled to the drive shaft. A flexible prophy cup is mounted to the cup holder, and a bearing is rotatably disposed in the main passageway about the drive shaft. The bearing has a snap-lock element projecting into a recess provided in the housing, thereby fixing a longitudinal position of the bearing with respect to the housing and holding the drive shaft in driving engagement with the cup holder. The prophy cup is coupled to the cup holder via a ball and socket joint and is provided in a region about the ball and socket joint with a flexible skirt defining an annular groove, the cup holder having an annular seat projecting into the groove. The seat preferably has an outer surface inclined at an angle with respect to a longitudinal axis of the cup holder. The skirt engages the outer surface of the seat and bends upon such engagement during use of the prophylaxis angle. In addition, the prophy cup is provided with outwardly extending projections in the groove, the seat being formed with inwardly extending teeth meshing with the projections for driving the cup. The prophy cup may also include on the interior of its flexible skirt a retaining extension that is held by an opposing retaining base of the cup holder.

26 Claims, 7 Drawing Sheets

DENTAL PROPHYLAXIS ANGLE AND A PIVOTABLE PROPHY CUP THEREFORE

RELATED APPLICATION

This is a continuation-in-part of U.S. patent application Ser. No. 08/718,750, filed Sep. 23, 1996 now abandoned.

BACKGROUND OF THE INVENTION

This invention relates to a dental prophylaxis angle.

Dental prophylaxis angles, known also as "Prophy Angles", are dental instruments used for rotatably holding dental tools such as brushes or prophy cups having receptacles which hold a dental prophy composition for application to tooth surfaces with rotary motion.

These prophy angles typically include a body having a head at an angle relative to the body, most commonly 90 degrees. A drive shaft extends through the body to engage a drive gear incorporated in the angle for rotatably driving a tool located on the head. The body is attached to a handpiece which connects the drive shaft to a remotely located motor.

Because of its use in the mouth, the prophy angle must be either sterilizable or disposable, and a single use disposable angle is preferred. Consequently, a low cost yet reliable prophy angle is needed.

Various disposable prophy angles are known such as those described in U.S. Pat. Nos. 5,156,547, 5,040,978, or 5,028,233, among other. However, in each case, the number of parts and degree of complexity in assembly result in increased costs.

It is also desirable to provide prophy angles which incorporate a bend in a neck portion of the housing to facilitate movements within the mouth. However, many of the existing prophy angles are not easily modified by incorporating such a bend due to conflicts with the bearing system or other drive components. For example, the prophy angle of U.S. Pat. No. 5,040,978 includes an enlarged shaft portion which cannot tolerate such a bend.

It is also desirable to assure access to all tooth surfaces, particularly interproximal surfaces. Most disposable prophy angles currently on the market have a short cup rigidly mounted to a rotatable cup holder. In order to reach all dental surfaces, the clinician must work the dental handpiece back and forth and at various angles while applying considerable pressure to conform the cup to the tooth surfaces. In addition to patient discomfort, such use may give rise to repetitive movement injuries such as carpal tunnel syndrome.

One known disposable prophylaxis angle currently on the market has a relatively long prophy cup. Although this design increases cup flexibility, the larger size of the cup and associated prophy angle head makes it more difficult to treat all tooth surfaces and increases discomfort as the dentist maneuvers the large cup and angle within the mouth.

SUMMARY OF THE INVENTION

It is an object of the present invention to provide a dental prophylaxis angle having a prophy cup which conforms well to tooth surfaces and has good interproximal access.

Another object of the present invention is to provide a dental prophylaxis angle which is easy to use, for example, which the clinician need not constantly reposition to align the cup to the angled tooth surfaces.

A further object of the present invention is to provide a short prophy cup with enhanced flexibility.

Yet another object of the present invention is to provide a disposable prophylaxis angle having a simplified structure with a minimum number of parts for ease in assembly to reduce costs.

These and other objects of the invention are achieved by a dental prophylaxis angle comprising a unitary housing defining a main passageway and an ancillary passageway extending at a substantial angle thereto. A drive shaft extends through the main passageway, with a cup holder rotatably disposed in the ancillary passageway, the cup holder being drivingly coupled to the drive shaft. A bearing is rotatably disposed in a forward end of the main passageway about the drive shaft, the bearing having a flexible snap-lock tab containing an element which projects into a recess provided in the housing, thereby fixing the bearing with respect to the housing and holding the drive shaft in driving engagement with the cup holder.

The bearing serves to hold the position of the drive shaft with respect to the driven cup holder, but is sufficiently short to allow a neck portion of the housing to be bent by from about 5 to 15 degrees. Moreover, the snap-lock coupling of the bearing to the housing facilitates assembly of the prophylaxis angle.

Preferably, an inner end of the drive shaft is provided with a widened portion in sliding engagement with the bearing. The bearing and the widened shaft portion cooperate to hold the drive shaft in position against the cup holder.

The drive shaft is preferably drivingly connected to the cup holder via meshing gears on the drive shaft and the cup holder. The drive shaft has a longitudinal extension which projects forward from the widened shaft portion which is received in a groove in the cup holder. This serves in part to limit axial displacement of the drive shaft, and also to prevent removal of the cup holder from the ancillary passage.

In accordance with another optional feature of the present invention, an inner surface of the housing along the main passageway is provided with a groove longitudinally aligned with the recess for facilitating an insertion of the snap-lock element into the recess. After insertion, the relatively hollow neck portion of the housing can be bent, without interfering with the drive components.

In accordance with another embodiment of the present invention, the prophy cup has a spherical pocket for receiving a ball extending from the cup holder and a tapered passage leading to the pocket for coupling to the cup holder via a ball and socket joint. The cup additionally has a flexible skirt defining an annular groove about the ball joint, the cup holder having an annular seat which projects into the groove. The seat preferably has an outer surface inclined at an angle with respect to a longitudinal axis of the cup holder. Gaps are provided between the opposed upper and lower surfaces of the cup holder and prophy cup, respectively, to allow tilting of the prophy cup about the ball joint in use. The flexible skirt engages the outer surface of the seat and bends over the inclined surface during use of the prophylaxis angle, to provide conformance of the cup to contoured tooth surfaces, without altering the angle of the head. After disengagement, the skirt prompts the cup to return to its upright position, while also preventing pinching of soft mouth tissue between the cup holder and the prophy cup.

The dental prophylaxis angle is easy to use inasmuch as the clinician need not move the angle constantly to reposition the prophy angle to conform the cup to the tooth surfaces. In addition, since the cup is not long and conforms to the tooth surfaces almost automatically, less manually exerted pressure is needed, providing more comfort for the patient, less heat generated at the tooth surfaces and less clinician fatigue.

DESCRIPTION OF THE PREFERRED EMBODIMENTS

Figure 1:
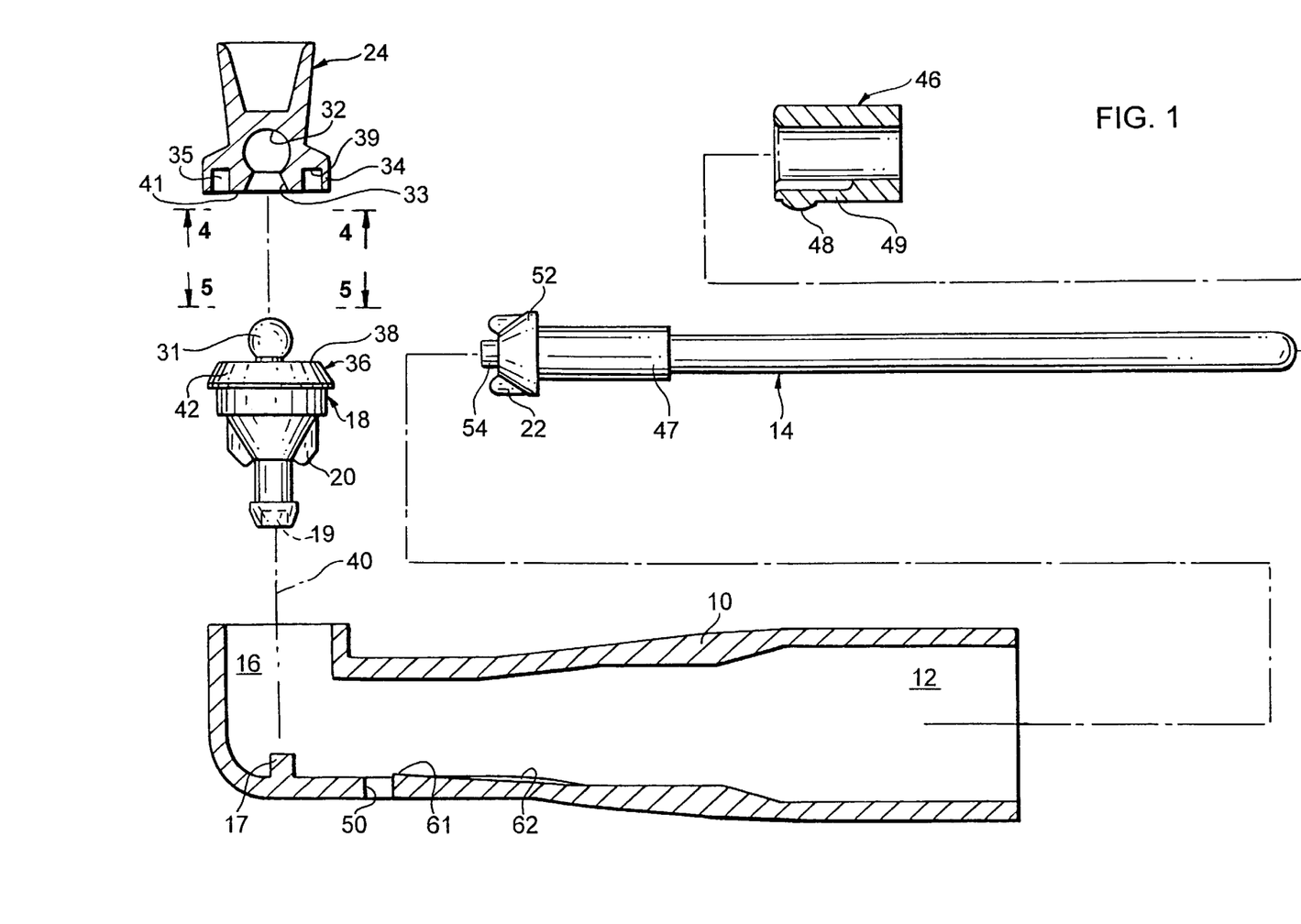
FIG. 1 is an exploded longitudinal cross-sectional view, on an enlarged scale, of a dental prophylaxis angle in accordance with the present invention.
Figures 2, 3:
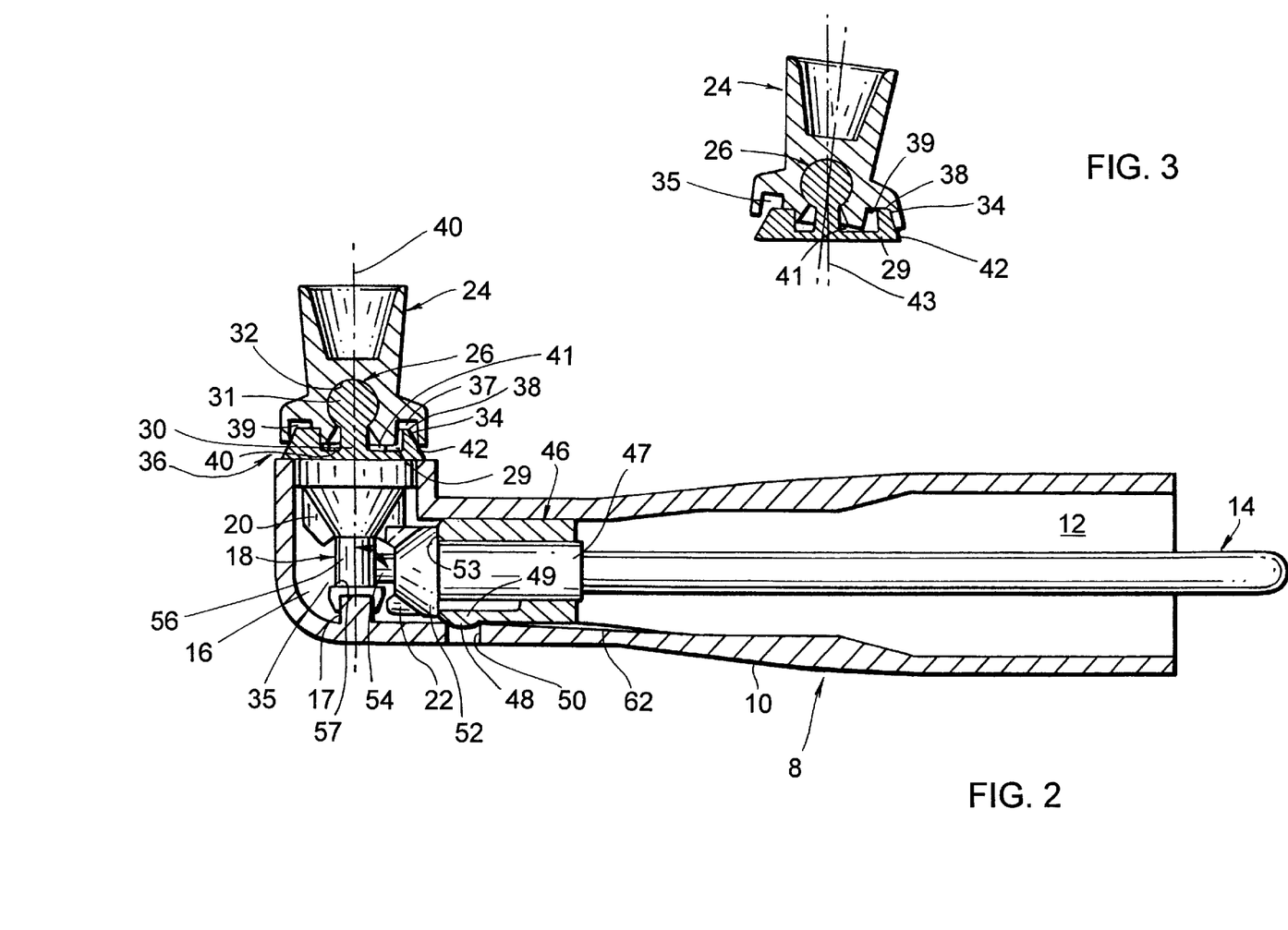
FIG. 2 is longitudinal cross-sectional view, on an enlarged scale, of the dental prophylaxis angle of FIG. 1, in an assembled configuration.
FIG. 3 is a cross-sectional view, on an enlarged scale, of the prophy cup and a portion of the cup holder of FIGS. 1 and 2, showing pivoting and deformation of the prophy cup during use.

Referring to FIGS. 1 and 2, a dental prophylaxis angle 8 comprises a unitary housing 10 defining a main passageway 12 which receives an elongated drive shaft 14. Housing 10 also defines an ancillary passageway 16 which communicates with the main passageway 12 and extends at an angle of 90 degrees relative thereto. A cup holder 18 is rotatably disposed in ancillary passageway 16. The cup holder 18 is rotatably retained in housing 10 in part via a cylindrical projection 17 which extends into an axial bore 19 in cup holder 18. The projection provides axial stability during rotation and assists in maintaining gear alignment. The cup holder 18 is provided with a plurality of gear teeth 20 which mesh with a plurality of gear teeth 22 on an inner end of drive shaft 4, to rotatably drive the cup holder.

A prophy cup 24 made of a flexible polymeric material is mounted to the cup holder 18 via a ball and socket joint 26. Cup holder 18 has a base 29 from which a post 30 extends having a ball 31 on the end. The ball 31 is received in a spherical pocket 32 in the prophy cup 24. A tapered passage 33 leads to the pocket, to ease insertion of the ball into the pocket. The tapered passage also allows a degree of tilt when using the prophy cup. The prophy cup 24 has a flexible cylindrical skirt 34 which surrounds an annular groove 35. The groove 35 receives an upwardly extending annular seat 36 of the cup holder 18, with a gap 37 provided between a top wall 38 of the seat and a base wall 39 of the groove. A second gap 40 is also provided between a lower surface 41 of the prophy cup and the base 29 when the ball is received in the pocket. The seat 36 has an outer surface 42 which is inclined at an angle with respect to a longitudinal axis 43 of the cup holder 18. As illustrated in FIG. 3, as the prophy cup 24 pivots about the ball 31, for example, when moving over a contoured tooth surface, the skirt 34 engages and slides over the inclined outer surface 42 of seat 36, until the top wall abuts the base wall, and the lower surface 41 abuts the base 29, thereby enhancing the flexibility of the prophy cup. 24, without jeopardizing cup stability, when the cup is removed from the tooth surface, the flexible skirt guides the cup to return to its upright position.

The prophy cup is made of a flexible material such as natural or synthetic rubber, silicone or another elastomer. The housing and cup holder are typically made of a rigid plastic, as is the bearing, and there are numerous materials available for producing these parts. The drive shaft is also produced of plastic, sufficiently rigid to transmit the rotational motion but having a degree of flexibility to accommodate the neck bend. One familiar with prophy angles can readily determine suitable materials for each component.

Figure 4:
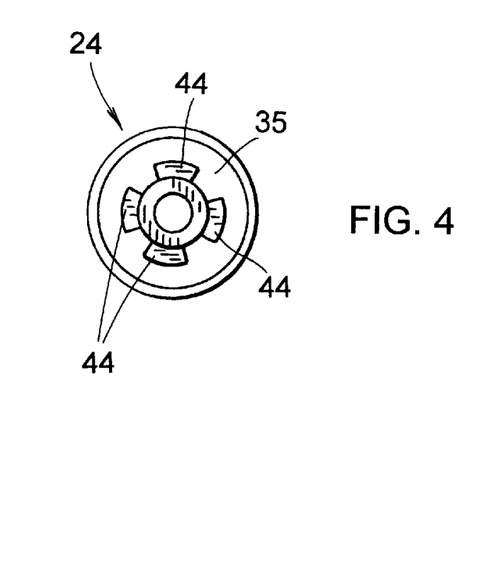
FIG. 4 is an end elevational view of the prophy cup of FIGS. 1–3, taken along line IV—IV in FIG. 1.
Figure 5:
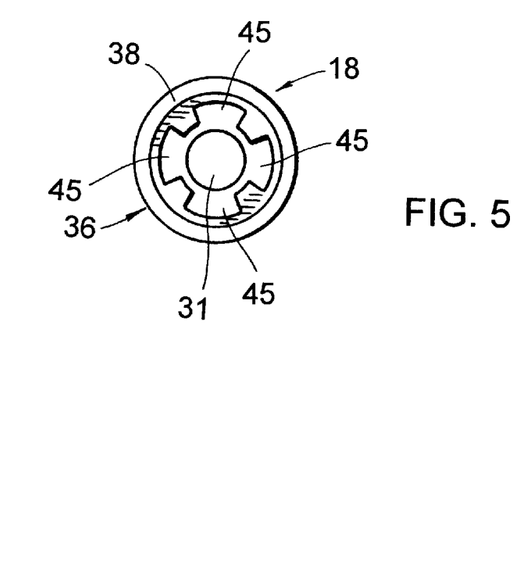
FIG. 5 is an end elevational view of the cup holder of FIGS. 1 and 2, taken along line V—V in FIG. 1.

As shown in FIGS. 1 and 4, prophy cup 24 is provided with four drive projections 44 which extend into the groove 35. As shown in FIGS. 1 and 5, the seat 36 is provided with four complimentary slots 45 for receiving the projections. The projections 44 engage the slots 45 in the manner of a gear coupling for transmitting rotary force from the cup holder 18 to prophy cup 24. The slots and projections are sized to accommodate tilting displacement without disengagement. That is, each component is of a sufficient length to allow displacement along the longitudinal axis during tilting without separation. This drive coupling enables the cup to tilt on the ball 31, thereby facilitating the pivoting of prophy cup 24 during use. Of course, the number and shapes of the projections and slots can vary, and the invention is not limited to the illustrated arrangement.

As illustrated in FIG. 2, a bearing 46 is rotatably disposed in the main passageway 12 about a bearing portion 47 of the drive shaft 14. The bearing 46 has a snap-lock element 48 projecting from a resilient tab 49 into a recess or aperture 50 provided in the housing 10. The snap-lock coupling of bearing 46 to housing 10 fixes the position of the bearing and holds the bearing stationary with respect to the housing while rotatably supporting the drive shaft 14.

The aperture is shown as a through passage to allow disassembly, if desired, by pressing in the locking element and pulling on the end of the drive shaft. Of course, if such disassembly is unnecessary, a depression type aperture rather than a through aperture may be used.

Gear teeth 22 extend from a widened portion 52 of the drive shaft 14. The widened portion 52 is held in position by an inner bearing surface 53. The bearing 46 and the widened shaft portion 52 cooperate to hold the drive shaft 14 in alignment with the cup holder gears 20. The position of the drive shaft 14 relative to the cup holder 18 is further maintained by a longitudinal extension 54 of the shaft 14. The extension 54 promotes meshing of gear teeth 20 and 22 by limiting movement of the drive shaft 14 towards the cup holder 18. Thus, the extension 54 and the bearing surface 53 cooperate to prevent axial movement of the drive shaft. The extension 54 also serves to prevent removal of the cup holder as it is received within a circumferential groove 55 about a stabilizing leg 56 of the cup holder. This leg contains the axial bore 19, and also has a step 57 which prevents removal of the cup holder through engagement with the extension 54.

Figure 6:
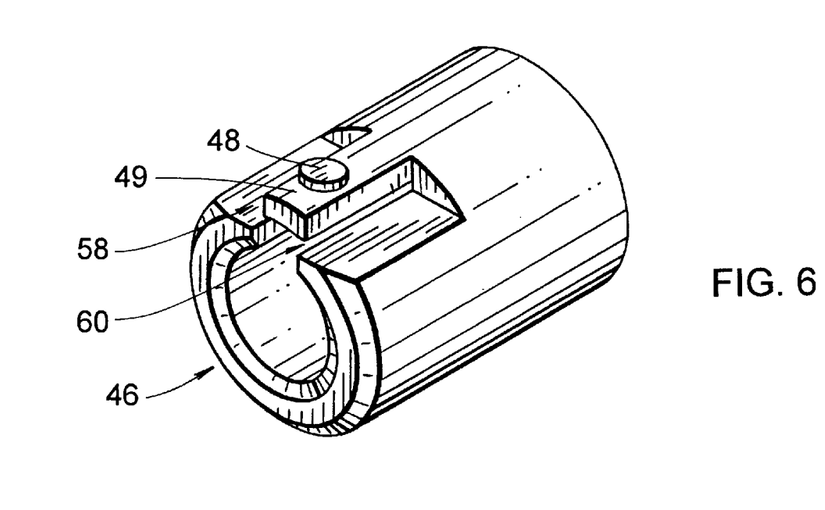
FIG. 6 is a perspective view, on an enlarged scale, of the bearing shown in FIGS. 1 and 2.

As illustrated in FIGS. 1, 2 and 6, the bearing 46 is formed with a longitudinally extending resilient tab 49 on which the snap-lock element 48 is disposed. The tab 49 is located between a pair of spaced longitudinally extending slots or cutouts 58 and 60 in bearing 46. In this embodiment, these slots are received by corresponding raised bosses 61 in the housing 10 which additionally has along the main passageway 12, a groove 62 longitudinally aligned with aperture 50 for facilitating insertion of the snap-lock element 48 into the recess. When the bearing is received in the housing, the tab is bent inwardly as it travels along the groove until the element 48 enters the aperture. This locks the bearing to prevent rotation or withdrawal, thus completing the assembly. However, it is not necessary to include the bosses and groove, as illustrated in FIG. 7.

The prophylaxis angle thus is produced with a minimum number of parts, that is, a unitary housing, a drive shaft, a bearing and a cup holder. Each part is integrally produced ready for assembly. First, the cup holder is placed in the passage way 16. The drive shaft is inserted until the gears engage and then the bearing is pushed into the housing, over the drive shaft until the element 48 snaps into the aperture 50. Thus, a single locking element holds all the components together.

An additional advantage of the invention, is that the bearing is forwardly located and relatively short and consequently, once assembled, the housing may be bent without interference with the drive components.

Figure 7:
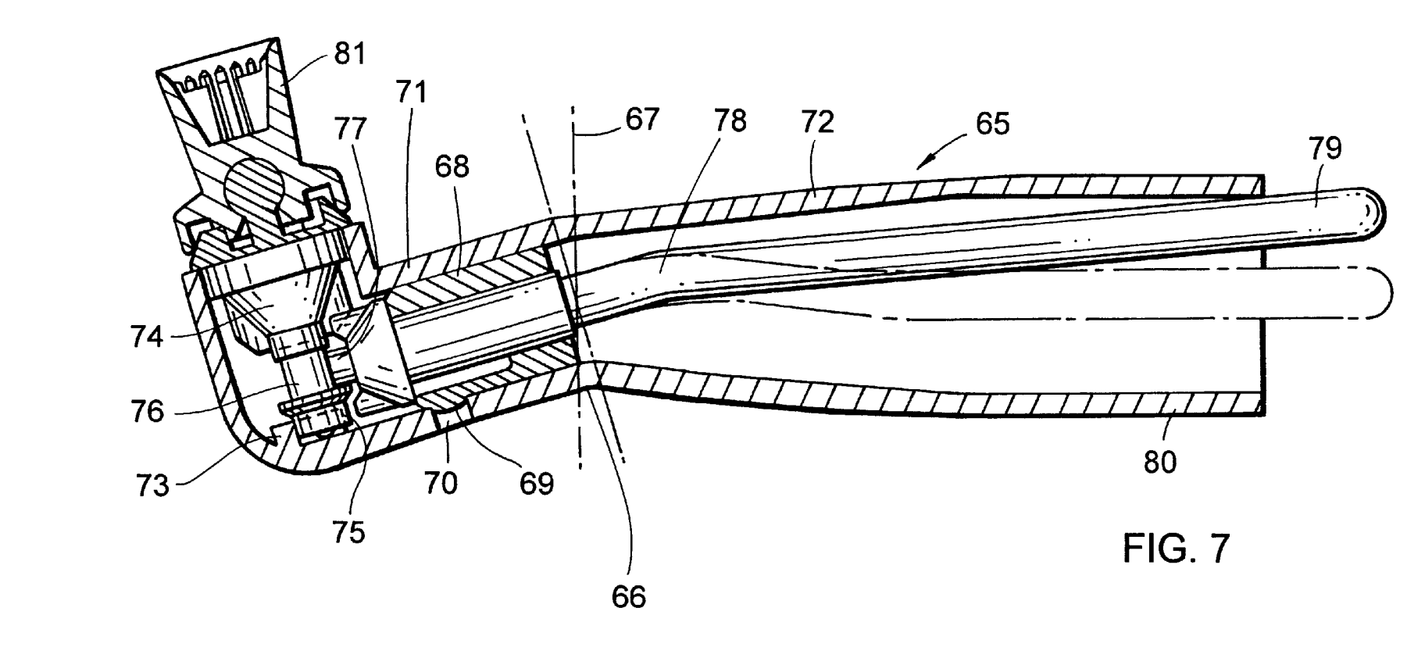
FIG. 7 is a longitudinal cross-sectional view, on an enlarged scale, of the dental prophylaxis angle with a bent neck.

Referring to FIG. 7, a prophy angle 65 has a bend 66 at an angle of about 15 degrees relative to the axis 67. The bend 66 is adjacent to a snap lock bearing 68 having a locking element 69 residing in a recess or aperture 70. The bearing resides in a forward bent portion 71 of a housing 72. In this housing, the optional longitudinal groove and raised bosses were not used.

Figure 7A:
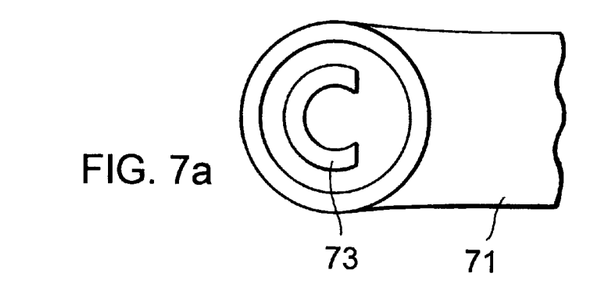
FIG. 7a is a top view showing the "c" shaped receptacle in the housing.

In this embodiment, an alternative to the post 17 was used for rotatably supporting the cup holder. Here, a "c" shaped receptacle 73 maintains the axial alignment of a cup holder 74 by surrounding a collar 75 on a stabilizing leg 76 of the cup holder. The "c" shaped receptacle is best seen in FIG. 7a. Again, this works in cooperation with an extension 77 on a drive shaft 78, to prevent removal of the cup holder from the housing.

The prophy angle 65 includes the drive shaft 78 which has an end 79 extending beyond an end 80 of the housing. This allows guidance of the end 79 into a hand piece (not shown) connected to a drive motor (not shown). These drive shafts are typically made of plastic and thus are easily bent with light pressure to the phantom position shown in FIG. 7a, for entry into the hand piece. The bearing 68 assures that despite the bend, proper rotational motion is transmitted to a prophy cup 81 mounted in the cup holder 74.

Figure 8:
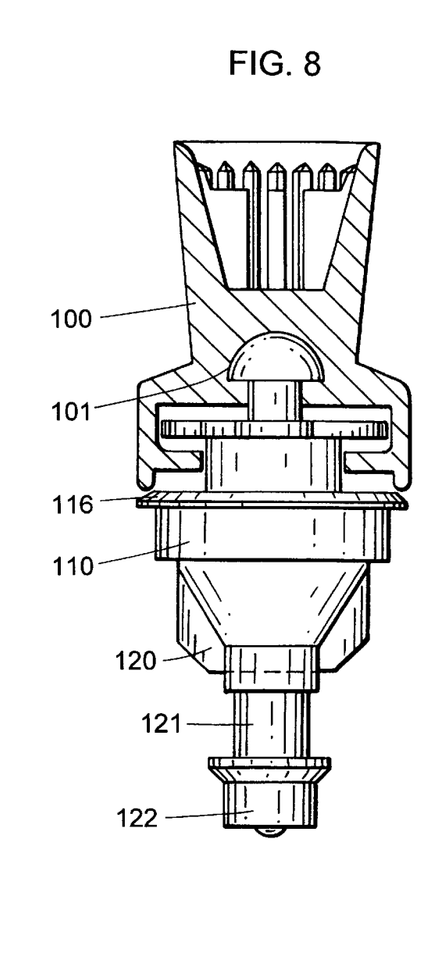
FIG. 8 is a view, on an enlarged scale, of the prophy cup and the cup holder in accordance with another embodiment of the present invention.

In accordance with another embodiment of the present invention, and referring now to FIG. 8, a modified cup holder 110 may be rotably disposed in ancillary passageway 16 of dental prophylaxis angle 8, shown in FIGS. 1 and 2, or of dental prophylaxis angle 65, shown in FIG. 7. Cup holder 110 is retained in the housing of the prophy angle and driven by means of the plurality of gear teeth 120, and supported by leg 121 and extension 122 in the same manner that cup holder 18 is driven and supported, as previously discussed. A modified prophy cup 100 made of the flexible polymeric material is mounted to cup holder 110 via socket joint 101. As seen more clearly in FIG. 9, cup holder 110 has a base 116 from which a first post 115 extends, on which a retaining base 114 is located. A second post 113 extends from retaining base 114, and post 113 has a semi-circular shaped head 112 on its end. The head 112 is received in a semi-circular pocket 102 of prophy cup 100. A tapered passage 103 leads to the pocket to ease insertion of head 112 into pocket 102. As will be discussed with reference to FIG. 10, a tapered passage also allows a degree of tilt when using prophy cup 100.

Figure 9:
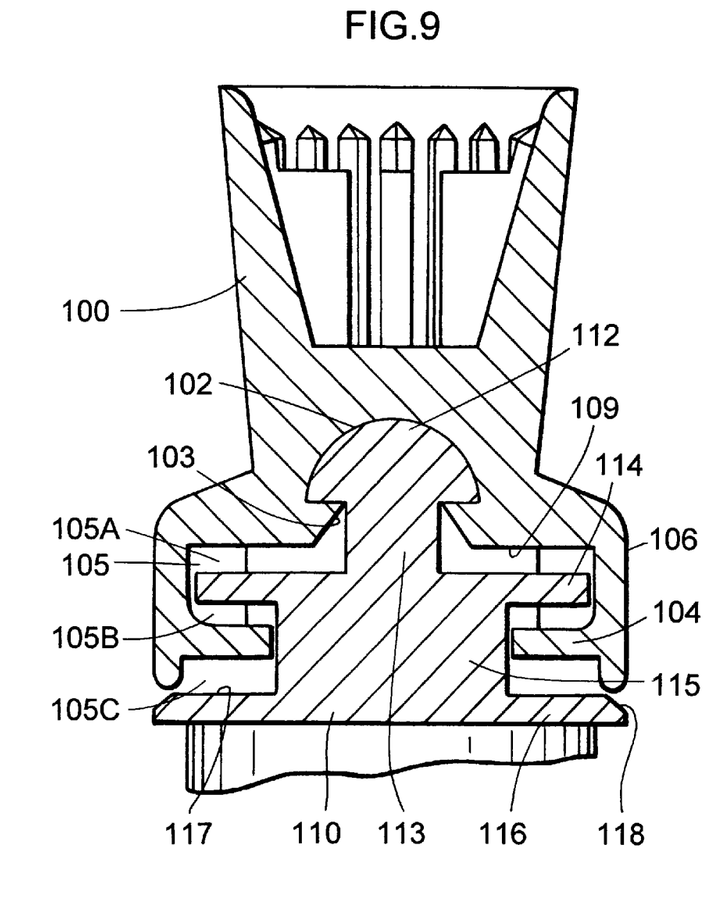
FIG. 9 is a cross-sectional view, on an enlarged scale, of the prophy cup and a portion of the cup holder of the embodiment shown in FIG. 8.
Figure 10:
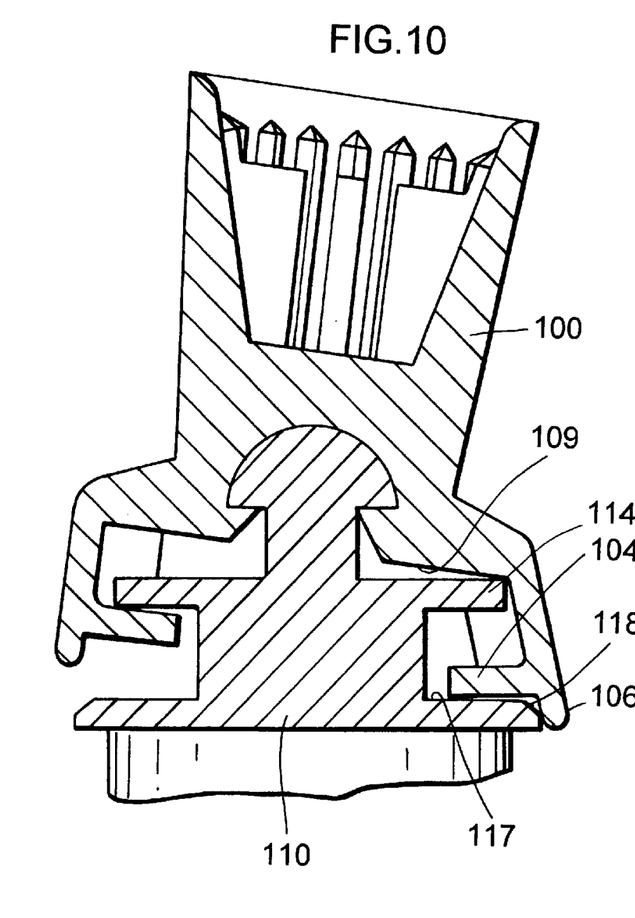
FIG. 10 is a cross-sectional view of prophy cup and cup holder shown in FIG. 8 showing pivoting and deformation of the prophy cup during use.

Prophy cup 100 has a flexible cylindrical skirt 106 on which on the interior side thereof extends a retaining extension 104. A groove 105 formed above retaining extension 104 within the interior of skirt 106 receives retaining base 114 of cup holder 110 upon insertion of head 112 into socket 102. In this position, upper and lower gaps 105A and 105B respectively are provided between retaining base 114 and a top surface 109 of the interior of prophy cup 100 and retaining base 114 and the top surface of retaining extension 104. Prophy cup 100 is made of a flexible material such as natural or synthetic rubber, silicone or other elastomer, cup holder 110 is typically made of rigid plastic, and thus insertion of retaining extension 104 past retaining base 114 as prophy cup 100 is inserted on cup holder 110 is facilitated by the flexibility of retaining extension 104. After full insertion of prophy cup 100 on cup holder 110, another gap 105C is provided between a lower surface of retaining extension 104 and the top surface 117 of base 116 of cup holder 110. As illustrated in FIG. 10, as prophy cup 100 pivots about head 1 12, skirt 106 engages and slides over an inclined surface 118 of base 116, until retaining base 114 abuts the top surface 109 of the interior of prophy cup 100, retaining extension 104 abuts the top surface 117 of base 116, and retaining base 114 abuts, and an opposite side, the top surface of retaining extension 104. By providing retaining base 114 in cup holder 110 and retaining extension 104 in prophy cup 100 in this embodiment, greater cup stability is provided while at the same time flexibility of prophy cup 100 is enhanced. When the cup is, for example, removed from a tooth surface, the flexible skirt 106 guides the cup to return to its upright position.

Figure 11:
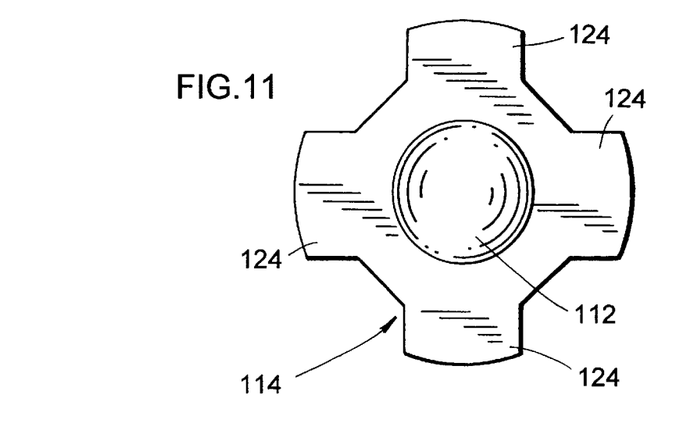
FIG. 11 is an elevational view of the cup holder shown in FIGS. 8–10.
Figure 12:
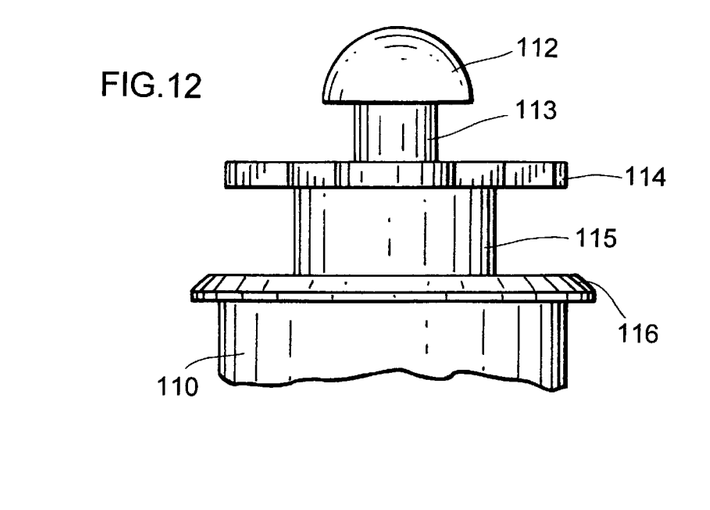
FIG. 12 is a side view of the cup holder of FIGS. 8–10.
Figure 13:
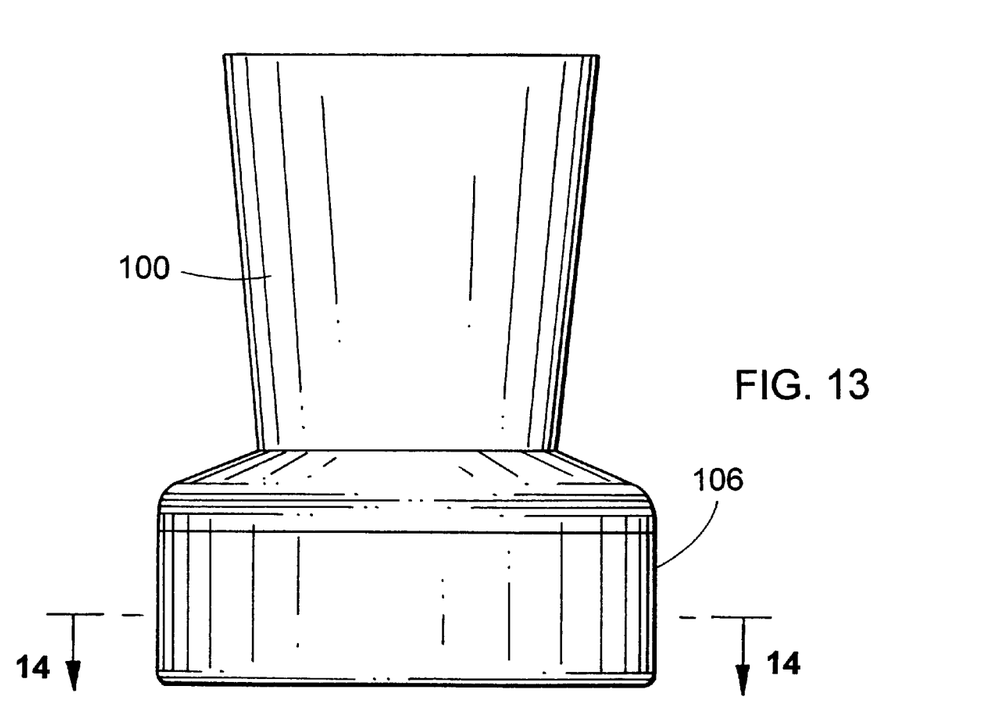
FIG. 13 is a side view of the prophy cup shown in FIGS. 8–10.
Figure 14:
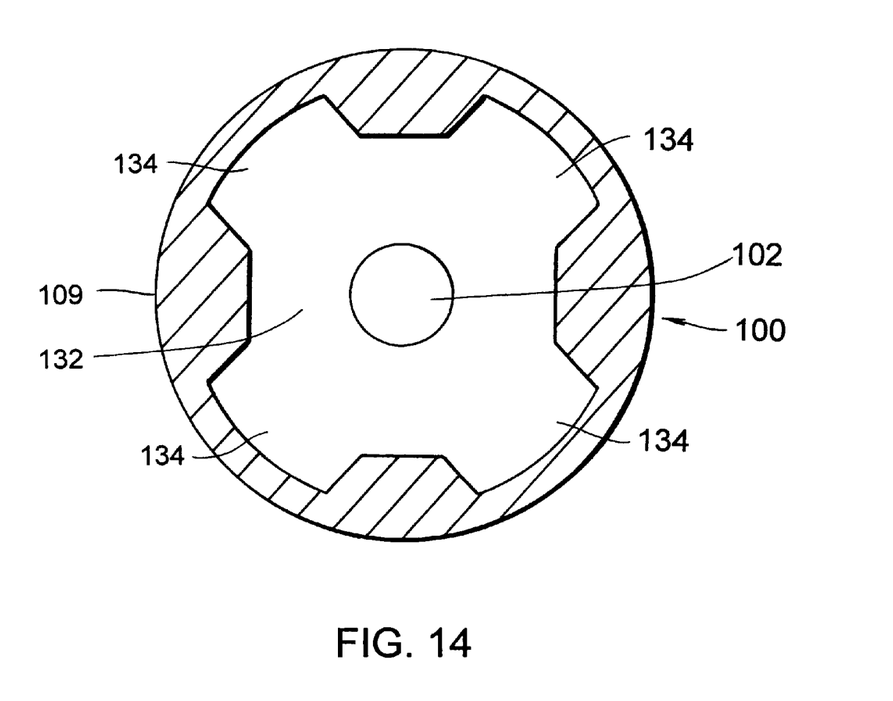
FIG. 14 is an elevational view of the prophy cup of FIGS. 8–10, taken along the line A—A in FIG. 13.

Referring now to FIGS. 11 and 12, retaining base 114 of cup holder 110 is somewhat plus shaped and includes four drive projections 124. As shown in FIG. 14, which is an elevational view of prophy cup 100 taken along line A—A shown in FIG. 13, the top surface 109 is formed to provide four complimentary slots 134, forming cut out 132, that receive the four drive projections 124 of cup holder 110. Projections 124 engage slots 134 in the manner of a gear coupling for transmitting rotary force from cup holder 110 to prophy cup 100. The slots and projections are sized to accommodate tilting displacement without disengagement. That is, each component is of a sufficient length to allow displacement along the longitudinal axis during tilting without separation. In one possible embodiment, the particular shape of cut-out 132 shown in FIG. 14 is provided along a depth of the interior of prophy cup 100 extending from the top surface 109 to retaining extension 104, thus ensuring that the gears never slip while retaining extension 104 is retained by retaining base 114. During such retainment, spaces 105A, 105B and 105C facilitate the pivoting of prophy cup 100 during use, as previously discussed. Spaces 105A and 105B are provided above and below, respectively, each of the four projections 124 on retaining base 114 of cup holder 110, within slots 134 of prophy cup 100. Of course, the numbers and shapes of the projections and slots can vary.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A dental prophylaxis angle comprising:
   a unitary housing defining a main passageway and an ancillary passageway extending from a forward end of the main passageway at a substantial angle thereto;
   a drive shaft located within the main passageway;
   a cup holder rotatably disposed in the ancillary passageway, the cup holder being drivingly coupled to the drive shaft; and
   a bearing removably disposed in the forward end of the main passageway and including an opening through which the drive shaft is rotatably positioned, the bearing having a flexible snap-lock tab containing an element which is locked into a recess provided in the housing, thereby fixing the bearing with respect to the housing and holding the drive shaft in driving engagement with the cup holder.

2. The dental prophylaxis angle of claim 1 wherein said drive shaft has a drive end located within the forward end of the main passageway and engaging said cup holder, said drive end having a widened portion in contact with a forward surface of said bearing proximal to the forward end of the main passageway.

3. The dental prophylaxis angle of claim 2 wherein said drive shaft is drivingly connected to said cup holder via meshing gear teeth on said drive shaft engaged to corresponding teeth on said cup holder, said drive shaft having an extension positioned within a circumferential groove about a leg of and extending from the cup holder to limit axial displacement of the drive shaft.

4. The dental prophylaxis angle of claim 1 wherein said tab is defined by a pair of spaced longitudinally extending slots in said bearing.

5. The dental prophylaxis angle of claim 1 wherein said housing has an inner surface along said main passageway, said inner surface having a groove longitudinally aligned with said recess for facilitating an insertion of said snap-lock element into said recess.

6. The dental prophylaxis angle of claim 1 wherein said cup holder has a base with an upwardly extending post, a ball located on the end of the post to provide a ball and socket joint, said cup holder having an annular seat with an inclined outer surface and spaced inwardly projecting gear portions for driving a tool mounted in the cup holder.

7. The dental prophylaxis angle of claim 1 wherein the housing has a neck portion extending from a rear end of the main passageway, the neck portion being bent at an angle of up to 15 degrees relative to the main passageway.

8. A dental prophylaxis angle comprising:
   an unitary housing defining a main passageway and an ancillary passageway extending at a substantial angle thereto;
   a drive shaft extending through said main passageway;
   a cup holder rotatably disposed in said ancillary passageway, said cup holder being drivingly coupled to said drive shaft; and
   a flexible prophy cup mounted to said cup holder, said prophy cup having a base, a cup structure for polishing the teeth extending upwardly from the base, the base having means for tiltably mounting to the cup holder, the cup holder having corresponding mounting means for engaging the prophy cup mounting means, said cup holder mounting means being a ball mated to a socket in said prophy cup base, wherein said prophy cup is coupled to said cup holder via a ball and socket joint, said prophy cup having a flexible skirt downwardly extending from the base, an annular groove defined between the flexible skirt and the socket, said cup holder having an annular seat projecting into said groove, gaps provided between a surface of the groove of the prophy cup and a surface of the seat of the cup holder to allow tilting of the prophy cup about the ball and socket joint in use.

9. The dental prophylaxis angle defined in claim 8 wherein said seat has an outer surface inclined at an angle with respect to a longitudinal axis of said cup holder, said skirt engaging said outer surface and bending upon over the inclined surface during use of the prophylaxis angle.

10. The dental prophylaxis angle defined in claim 8 wherein said prophy cup has drive projections extending into said groove, said seat having inwardly extending teeth which mesh with said projections for driving said cup.

11. The dental prophylaxis angle defined in claim 8 further comprising a bearing removably disposed in said main passageway about said drive shaft, said bearing having a snap-lock element projecting into a recess provided in said housing, thereby fixing a longitudinal position of said bearing with respect to said housing and holding said drive shaft in driving engagement with said cup holder, said drive shaft having an inner end engaging said cup holder, said inner end being provided with a widened portion in rotatable engagement with said bearing.

12. A dental method comprising:
   providing a dental prophylaxis angle wherein a flexible prophy cup is pivotably mounted to a cup holder which is in turned rotatably mounted to an angle housing, said prophy cup having a base, a cup structure for polishing the teeth extending upwardly from the base, the base having means for tiltably mounting to the cup holder, the cup holder having corresponding mounting means for engaging the prophy cup mounting means, wherein said prophy cup is provided with a flexible skirt downwardly extending from the base, an annular groove defined between the flexible skirt and the prophy cup mounting means, said cup holder having an annular seat projecting partially into said groove, defining a gap therebetween to allow tilting of the prophy cup relative to the cup holder, said seat having an outer surface upon the pivoting of said prophy cup with respect to said cup holder;
   depositing a dental prophy composition into said prophy cup;
   placing said prophy cup with the deposited dental prophy composition against a tooth surface;
   rotating said cup holder and concomitantly said prophy cup while moving said prophy cup with the deposited dental prophy composition along said tooth surface;
   during the movement of said prophy cup with the deposited dental prophy composition along said tooth surface, said prophy cup pivoting with respect to said cup holder so that an axis of said prophy cup is oriented at a substantial angle relative to an axis of said cup holder; and
   bending said skirt against said outer surface during an engagement of said skirt with said outer surface upon the pivoting of said prophy cup with respect to said cup holder.

13. A dental prophylaxis cup for mounting to a cup holder having means for accepting the prophy cup thereon, the prophy cup comprising a base, a cup portion extending upwardly from the base and having a receptacle for accepting a prophy composition therein, a lower portion extending downwardly from the base, the lower portion including means for tiltably mounting to the cup holder, a flexible skirt projecting downwardly from the base and surrounding the means for mounting to the cup holder, an annular groove defined therebetween, such that the groove accepts a seat of the cup holder therein, a gap between an upper surface of the seat and a bottom wall of the groove accommodating tilt of the prophy cup, the flexible skirt slidable over an outer surface of the cup holder to bias the prophy cup into an upright position.

14. The prophy cup of claim 13 further comprising a plurality of spaced drive projections extending into the groove for engaging corresponding recesses in the cup holder.

15. The prophy cup of claim 13 wherein the means for tiltably mounting the prophy cup to the cup holder is a socket in the lower portion and a tapered passage leading to the socket, said socket and tapered passage receiving the cup holder mounting means therein.

16. The prophy cup of claim 15 wherein the tapered passage has a lower surface, a gap provides between the lower surface and a base of the cup holder to allow tilting of the prophy cup in use.

17. A dental prophylaxis angle comprising:
  an unitary housing defining a main passageway and an ancillary passageway extending from a forward end of the main passageway at a substantial angle thereto;
  a drive shaft extending through said main passageway;
  a cup holder rotatably disposed in said ancillary passageway, said cup holder being drivingly coupled to said drive shaft; and
  a flexible prophy cup mounted to said cup holder, said prophy cup having a base, a cup structure for polishing the teeth extending in an upward direction from the base, the prophy cup including a lower portion having coupling means for rotatable and tiltably coupling said flexible prophy cup to said cup holder, said prophy cup having a flexible skirt downwardly extending from said base, and an annular retaining extension extending radially inwardly from an interior surface of said flexible skirt, said cup holder having a retaining base that project radially outwardly, the retaining base being received by said retaining extension such that when said prophy cup and said prophy cup holder are coupled, a gap is provided between a surface of said retaining base of the cup holder and a surface of said retaining extension of said prophy cup to allow tilting of the prophy cup about the coupling means.

18. The dental prophylaxis angle of claim 17, wherein said cup holder has a first base with a first upwardly extending post thereon, said retaining base is located on an end of said first post, said retaining base has a second post extending upwardly thereon, and a head is disposed on an end of said second post; and said coupling means of said prophy cup is a pocket for receiving said head of said cup holder.

19. The dental prophylaxis angle of claim 18, wherein a gap is provided between a surface of said retaining extension of said prophy cup and said first base of said cup holder to further allow tilting of the prophy cup about the coupling means.

20. The dental prophylaxis angle of claim 18, wherein said first base has an outer surface inclined at an angle with respect to a longitudinal axis of said cup holder, said flexible skirt engaging said outer surface and bending upon over the inclined surface during use of the prophylaxis angle.

21. The dental prophylaxis angle of claim 17, wherein a gap is provided between a top surface of said retaining base and a top surface of an interior of said prophy cup defined by said flexible skirt to further allow tilting of the prophy cup.

22. The dental prophylaxis angle of claim 17, wherein said retaining base of said cup holder has drive projections for driving said prophy cup; and an interior of said flexible skirt of said prophy cup has slots at positions corresponding to said drive projections for receiving said drive projections.

23. A dental prophylaxis angle, comprising:
  a housing;
  a drive shaft extending through said housing;
  a cup holder rotatably disposed in said housing, said cup holder being drivingly coupled to said drive shaft; and
  a flexible prophy cup mounted to said cup holder, said prophy cup including coupling means for rotatably and tiltably coupling said flexible prophy cup to said cup holder, said coupling means being adapted to tilt on said cup holder.

24. The dental prophylaxis angle of claim 23, wherein said cup holder includes retaining means that is adapted to tiltably couple to said coupling means of said prophy cup in a plurality of directions so that said prophy cup is slanted with respect to said cup holder when said prophy cup is tilted during use.

25. The dental prophylaxis angle of claim 23, wherein said prophy cup includes a bottom surface below said coupling means of said prophy cup, and said cup holder includes a surface facing the mounted prophy cup, and said bottom surface of said prophy cup is not in contact with said surface of said cup holder when said prophy cup is not tilted with respect to said cup holder, and a portion of said bottom surface approaches a portion of said surface of said cup holder as said prophy cup is tilted.

26. A dental method comprising the steps of:
  providing a dental prophylaxis cup for mounting to a cup holder having means for mounting the prophy cup thereon, the prophy cup having a base, a cup portion extending upwardly from the base and having a receptacle for receiving a prophy composition therein, a lower portion extending downwardly from the base, the lower portion including means for tiltably mounting to the cup holder, a flexible skirt projecting downwardly from the base and surrounding the means for mounting to the cup holder, an annular groove defined therebetween, the groove accepting a seat of the cup holder therein, a gap between an upper surface of the seat and a bottom wall of the groove accommodating tilt of the prophy cup, the flexible skirt slidable over an outer surface of the cup holder to bias the prophy cup into an upright position;

providing a dental prophylaxis angle having a prophy cup holder for mounting the flexible prophy cup thereto, the cup holder having means for coupling to the prophy cup and having a seat for receiving the prophy cup, the annular groove of the prophy cup having a depth sufficient to provide a gap between an upper surface of the seat and a bottom wall of the groove;

depositing a dental prophy composition into said receptacle of said prophy cup;

placing said prophy cup with the deposited dental prophy composition against a tooth surface;

rotating said prophy cup and moving said prophy cup along said tooth surfaces and, said prophy cup tilting with respect to said cup holder so that the prophy cup receptacle adapts to the contacted tooth surface.

* * * * *